United States Patent [19]

Kunig

[11] Patent Number: 4,987,901

[45] Date of Patent: Jan. 29, 1991

[54] METHOD AND APPARATUS FOR SELECTING A PHYSIOLOGICALLY STANDARDIZED SENSOR OF A MULTI-SENSOR ELECTROCARDIOGRAM SENSOR SET

[76] Inventor: Horst E. Kunig, R.D. #1, Box 577, Saltsburg, Pa. 15681

[21] Appl. No.: 373,227

[22] Filed: Jun. 28, 1989

[51] Int. Cl.$^5$ .................. A61B 5/0456; A61B 5/0452
[52] U.S. Cl. ..................................... 128/696; 128/704
[58] Field of Search ............... 128/704, 708, 700, 713, 128/716, 718, 696, 671, 698

[56] References Cited

U.S. PATENT DOCUMENTS

| | | | |
|---|---|---|---|
| 3,554,187 | 1/1971 | Glassner | 128/706 |
| 3,572,321 | 3/1971 | Bloomfield et al. | 128/704 |
| 4,622,980 | 11/1986 | Kunig | 128/704 |
| 4,754,762 | 7/1988 | Stuchl | 128/704 |

FOREIGN PATENT DOCUMENTS

| | | | |
|---|---|---|---|
| 0167202 | 11/1950 | Austria | 128/696 |
| 2758347 | 6/1978 | Fed. Rep. of Germany | 128/696 |

*Primary Examiner*—William E. Kamm
*Assistant Examiner*—Kennedy J. Schaetzle
*Attorney, Agent, or Firm*—Clifford A. Poff

[57] ABSTRACT

A method and apparatus for identifying physiologically standardized electrode positions from a multisensor electrocardiogram electrode sensor set. The P-, Q-, R-, S-, and T-wave components of each of the electrocardiogram waveforms are compared, and the sensors corresponding to the waveform containing the P-, Q-, R-, S, and T-wave components of the greatest magnitudes are selected as the standardized electrode positions.

18 Claims, 3 Drawing Sheets

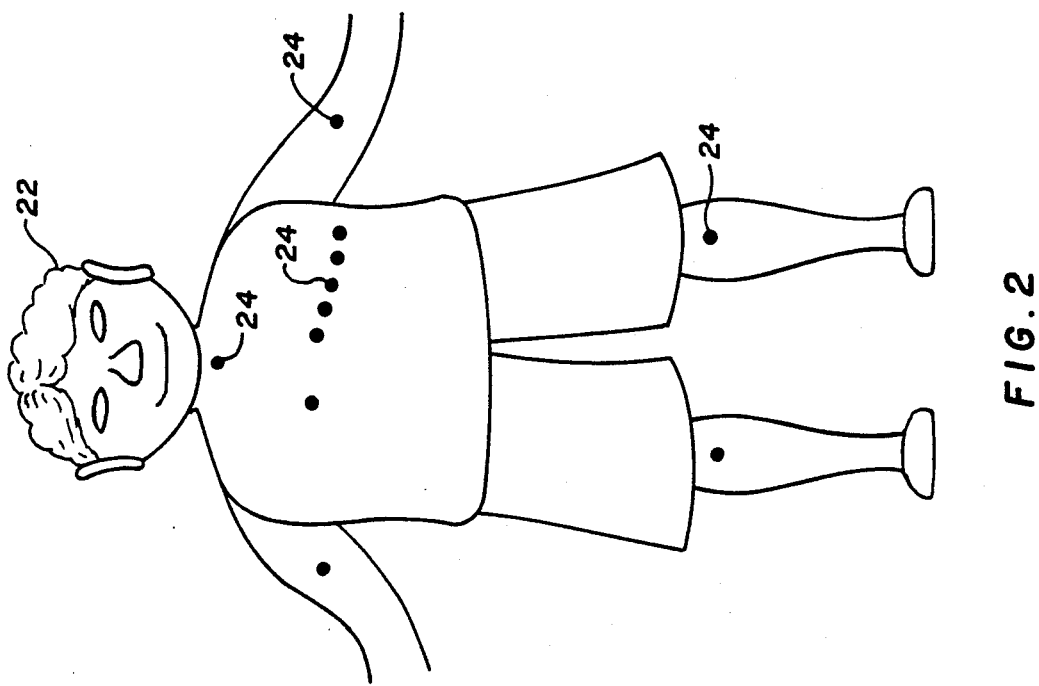
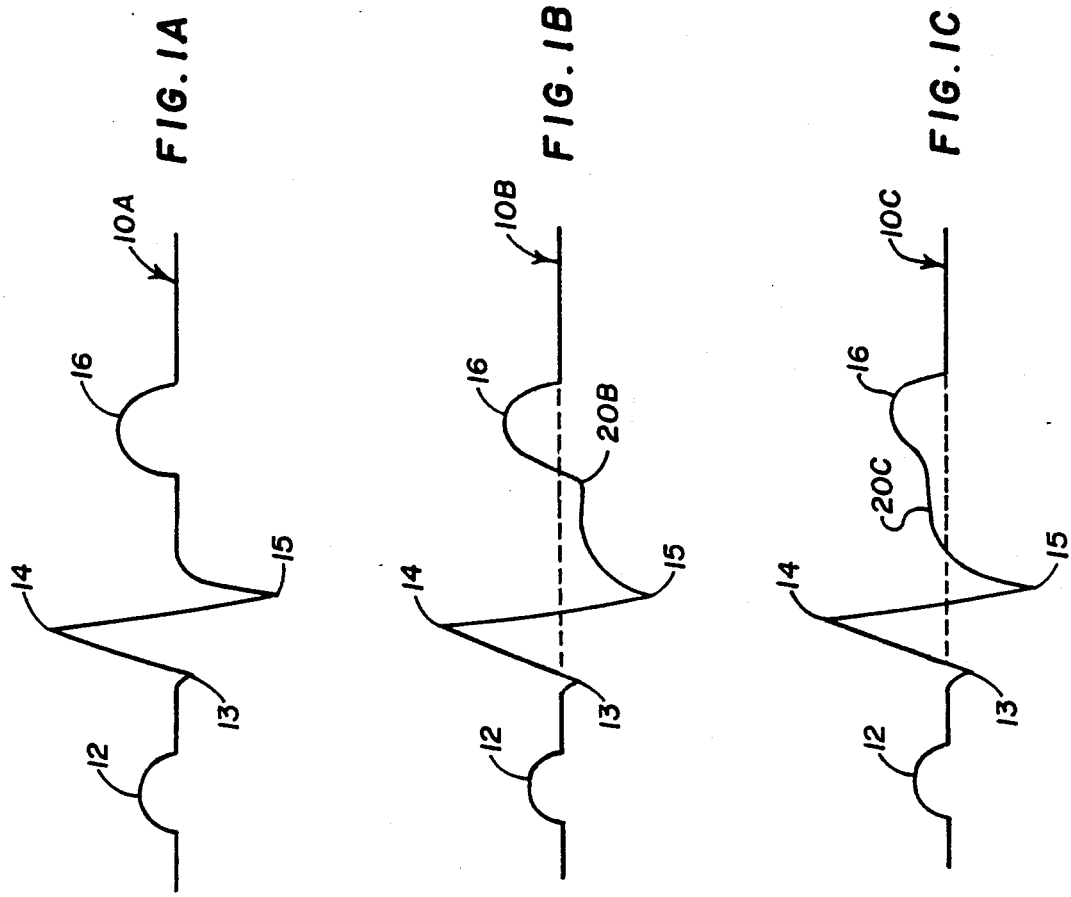

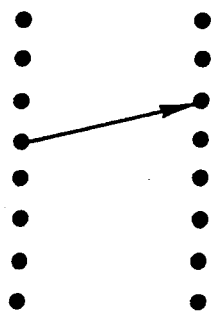 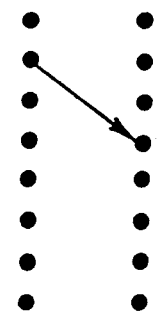
FIG.5A   FIG.5B
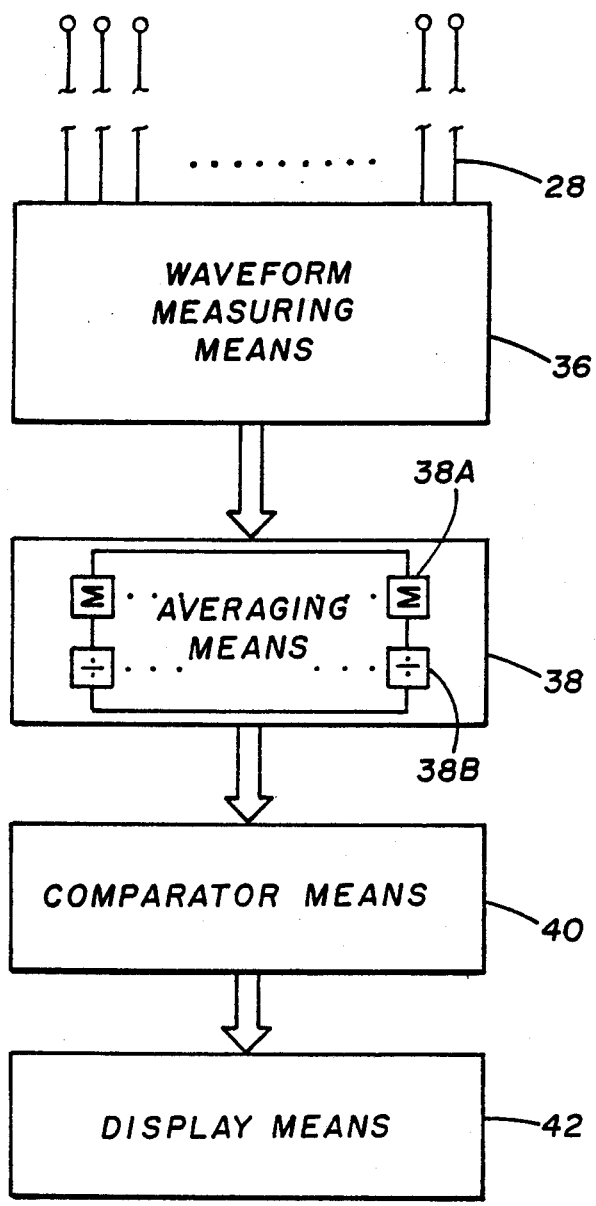
FIG.6

METHOD AND APPARATUS FOR SELECTING A PHYSIOLOGICALLY STANDARDIZED SENSOR OF A MULTI-SENSOR ELECTROCARDIOGRAM SENSOR SET

BACKGROUND OF THE INVENTION

1. Field of the Invention

The present invention relates generally to electrocardiographic apparatus, and, more particularly, to a method and apparatus for selecting a sensor pair forming a lead from a multi-sensor electrocardiogram sensor set to be a physiologically standardized lead to monitor the electrocardiographic performance of an individual.

2. Description of the Prior Art

A fundamental tool used to monitor and diagnose cardiovascular functioning of an individual is the electrocardiogram. An electrocardiogram is the plot of the waveform created by electrical signals generated by the cardiac functioning of an individual. The signals are actually indications of depolarization and repolarization of cardiac tissue. These electrical signals are detected by electrical contact sensors placed on the individual, and the signals detected by the sensors are plotted. The resultant waveforms are then analyzed in order to evaluate the cardiovascular performance of the individual.

Typically, ten electrocardiogram sensors are positioned at different locations on the individual with the specific locations being selected for geometric considerations. Several of the sensors are bipolar which are placed on the arms and legs (i.e., the extremities) of the individual, and the remaining sensors are unipolar and are placed on the chest area of the individual. The unipolar sensors are referenced with respect to intercoastal space, a midclavicular line, an anterior axillary line, and a midaxillary line. In these positions, the bipolar and unipolar sensors are referred to as being in a geometrically standardized placement.

A significant problem inherent in the use of electrocardiograms is that the resulting waveforms are position determinative, that is to say, the signals sensed by a sensor are dependent on where the sensor is positioned on the individual's body.

In fact, this variance is the reason why a plurality of sensors (i.e., ten for a standard twelve lead electrocardiogram) are utilized. By increasing the number of sensors, the chances that a medically significant signal might be missed is reduced. However, a diagnosis based upon a reduced chance of missing a medically significant signal is still ambiguous, and may place a patient at risk.

It is therefore a customary practice to employ average values derived by calculating average values of all the waveforms obtained from all of the sensors. However, this practice results in a diagnosis being made based upon average values; such a diagnosis may still be ambiguous or inaccurate.

It is therefore an object of the present invention to provide a method and apparatus for selecting an electrode sensor pair to be a physiologically standardized electrode pair from the multi-sensor electrocardiogram electrode sensor set from which analysis of the cardiac functioning of an individual may be performed. Accordingly, a physiologically standardized electrode sensor pair is defined as that pair which generates the largest waveform component, i e., the largest R-wave amplitude, T-wave amplitude, P-wave amplitude, Q-wave amplitude, or S-wave amplitude.

It is a further object of the present invention to provide a set of electrocardiogram sensors positioned in a preconstructed unit such that the sensors are maintained at defined distances from one another to allow a sensor pair to be selected from the set to be utilized as a physiologically standardized electrode pair.

For example, depolarization is the physiological principle for the creation of the R-wave component and repolarization is the physiological principle for the T-wave component of an electrocardiogram . By placing electrode sensor pairs in a physiologically standardized manner on two or more subjects the maximum component waveforms R and T for all subjects can then be measured and compared. As a corollary, the underlying physiological principles for the creation of the component waveforms can be compared and diagnostically analyzed. It is therefore a further object of this invention to provide physiologically standardized electrode sensor pairs for diagnostic analysis of physiological phenomena responsible for the creation of waveform components of an electrocardiogram. Geometrically standardized electrode sensor pairs do not permit such a comparison of the physiological phenomena.

SUMMARY OF THE INVENTION

In accordance with the present invention, an electrocardiographic apparatus for selecting a desired number of physiologically standardized sensors of a plurality of electrocardiogram sensors comprising a multi-sensor electrocardiogram sensor set to allow diagnosis of cardiac performance of an individual is disclosed. The apparatus includes a plurality of electrocardiogram sensors positioned on the individual for sensing electrocardiogram waveforms indicative of the cardiac functioning of the individual, waveform measuring means coupled to receive the electrocardiogram waveforms sensed by each of the electrocardiogram sensors of the plurality of electrocardiogram sensors for measuring magnitudes of predetermined components of the electrocardiogram waveforms. A comparator means compares the magnitudes of the predetermined components of the electrocardiogram waveforms measured by the waveform measuring means and sensed by each of the plurality of electrocardiogram sensors, and determines the electrocardiogram waveforms, and hence, the electrocardiogram sensors, and the respective positions thereof on the individual at which the electrocardiogram waveforms are sensed containing the predetermined components of the greatest magnitudes, such positions on the individual corresponding to the physiologically standardized electrocardiogram sensor positions. A primary display means is further included for displaying the electrocardiogram waveforms selected by the comparator means.

In a preferred embodiment of the present invention, the waveform measuring means measures the magnitudes of the predetermined components during successive heartbeats and forms average values of the magnitudes of the predetermined components of each of the electrocardiogram waveforms. The comparator means may then compare the average values formed by the waveform measuring means and select the electrocardiogram waveforms containing the average predetermined components of the greatest magnitudes.

The predetermined components measured by the waveform generating means may include the P-, Q-, R-, S-, and/or T-wave components of the electrocardiogram waveforms.

The method according to the present invention for obtaining a physiologically standardized electrocardiogram sensor position to allow diagnosis of cardiac performance of an individual from a pair of electrocardiogram sensors includes the steps of: positioning a plurality of electrocardiogram sensors on the individual for sensing electrocardiogram waveforms indicative of cardiac functioning of the individual; measuring magnitudes of P-, Q-, R-, S-, and T-wave components of the electrocardiogram waveforms and respective averages from successive heartbeats detected by each of the plurality of electrocardiogram sensors; comparing magnitudes of the P-, Q-, R-, S-, and T-wave component of the electrocardiogram waveforms sensed by the electrocardiogram sensors; and selecting the electrocardiogram sensor pairs corresponding to electrocardiogram waveforms having the P-, Q-, R-, S-, and T-wave components of the greatest magnitudes as standardized electrocardiogram sensors, and the position thereof as the physiologically standardized electrocardiogram sensor position.

BRIEF DESCRIPTION OF THE DRAWINGS

The present invention will be better understood when read in light of the accompanying drawings in which:

FIGS. 1A–C illustrate sample waveforms detected by geometrically standardized electrocardiogram electrode sensors wherein FIG. 1A illustrates the electrocardiogram waveform of a healthy individual (i.e., a normal waveform), and FIGS. 1B and 1C illustrate waveforms having an ST-segment depression and elevation, respectively;

FIG. 2 illustrates the conventional, geometrically standardized position of placing ten electrocardiographic sensors; for recording a standard, twelve-lead electrocardiographic waveform pattern;

FIGS. 5A–B illustrate typical vectors which may be formed by the physiologically standardized sensor pairs selected by the apparatus of the present invention; and FIG. 6 is a block diagram of the electrocardiographic apparatus of the present invention.

DESCRIPTION OF THE PREFERRED EMBODIMENTS

Figure 4:
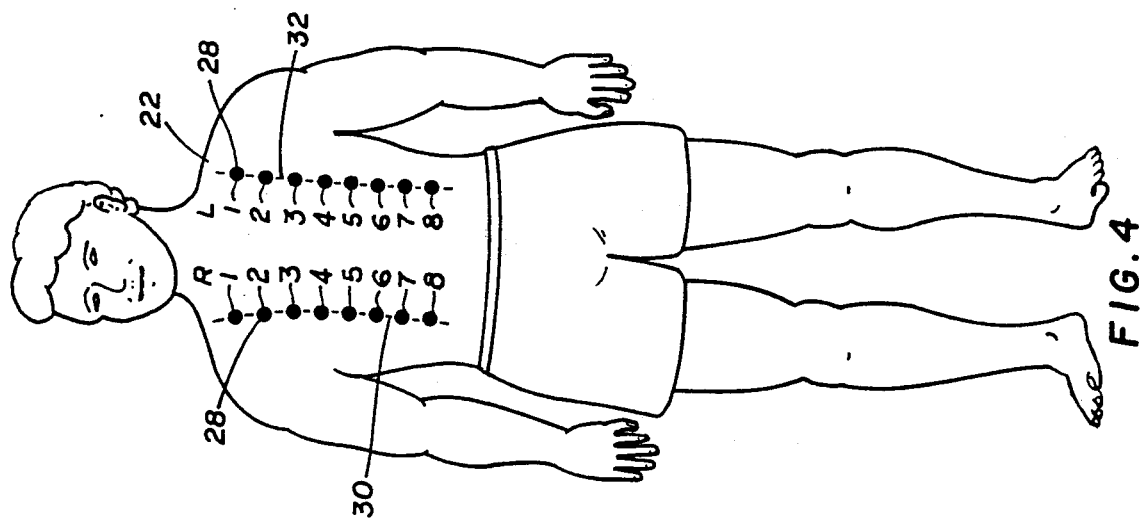
FIG. 4 illustrates the preferred placement of electrocardiographic sensors to record physiologically standardized electrocardiographic waveform patterns according to the present invention.

Referring first to FIGS. 1A–C, there are illustrated typical electrocardiogram waveforms 10A, 10B, and 10C which may be sensed by conventional electrocardiographic sensors. Each waveform is comprised of a number of component waves, P-wave component 12, Q-wave component 13, R-wave component 14, S-wave component 15, and T-wave component 16. As is well known in the art, the P-wave component and the QRS complex wave component are caused by depolarization of heart ventricles prior to their contraction. The T-wave component is caused by currents generated as the ventricles recover from depolarization. This is known as repolarization. Waveform 10A of FIG. 1A illustrates the electrocardiographic waveform of a healthy individual. Waveforms 10B and 10C of FIGS. 1B and 1C, respectively, are similar to waveform 10A but illustrate an ST-segment depression 20B in FIG. 1B and an ST-segment elevation 20C in FIG. 1C. Such ST-segment abnormalities are indicative of the cardiac disorder of myocardial ischemia.

As mentioned previously, because the individual sensors of an electrocardiographic sensor set are positioned at different body surface locations of the individual, different waveforms are detected by the leads formed by the different sensors. For example, two different leads formed by sensors positioned at two different locations on one individual may detect the waveforms of FIG. 1B and 1C, respectively, with the two waveforms having, as illustrated, an ST-segment depression 20B or elevation 20C of differing magnitudes. This variance causes a diagnosis of an individual's cardiac performance to be dependent upon which waveform is selected for analysis, and results in ambiguous conclusions as the position of the sensors from which the waveform is sensed is, at least in part, determinative of the resultant diagnosis. Additionally, the magnitudes of the detected waveforms are also dependent upon their position.

It is the purpose of the present invention, therefore, to provide a means and method for selecting a single electrocardiographic sensor pair to form a lead from which an analysis of an individual's cardiac performance may be made, to thereby reduce the ambiguity caused by differing, or contradictory, waveforms.

A typical geometry of positioning of a conventional multi-sensor electrocardiogram sensor setup for using geometric standardization is illustrated in FIG. 2 which shows an individual 22 upon which a plurality of electrocardiographic sensors 24 have been positioned in a conventional geometry. Each sensor 24 detects electrical signals wherein pairs of sensors 24 form leads to detect waveforms such as the waveforms 10A–C of FIGS. 1A–C.

Figure 3:
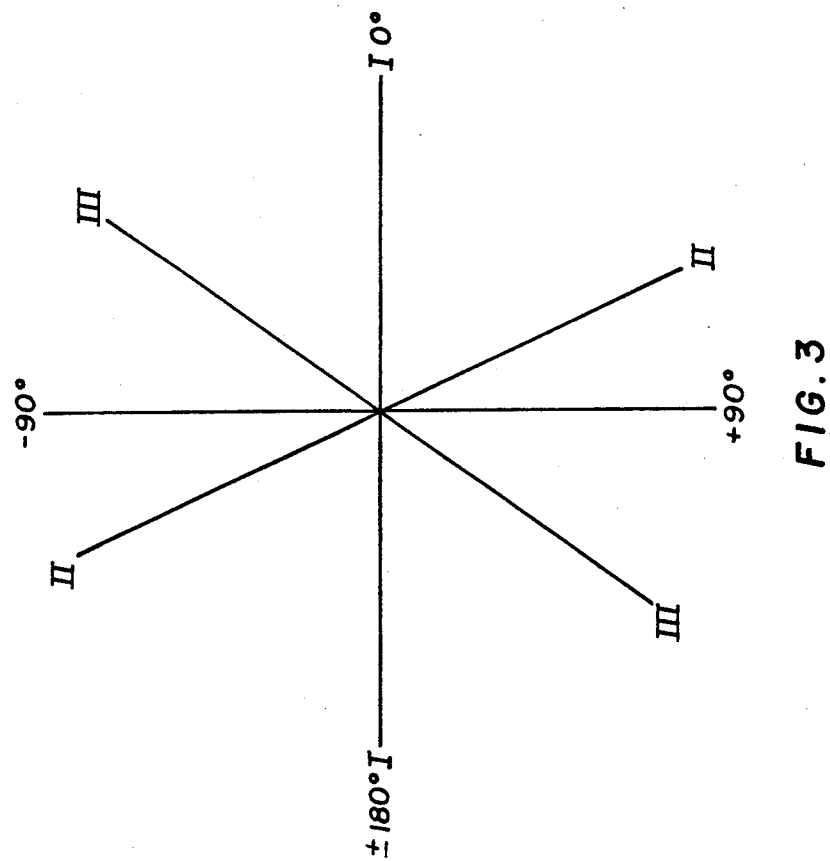
FIG. 3 illustrates the axis system frequently utilized to depict depolarization and repolarization of cardiac tissue during impulse transmission through the tissue.

Turning now to FIG. 3, there is shown standard vector nomenclature and axis system utilized to depict and describe depolarization and repolarization of cardiac tissue. By definition, a vector is characterized by magnitude and direction wherein the direction of the vector is defined by an angle. A zero reference point is centered above the heart upon the chest area of an individual such that a horizontal vector is defined to extend in a direction of zero degrees, and a vertical vector extends downwardly extending at ninety degrees. When a vector extends from left to right, it has a direction of one-hundred eighty degrees, and when a vertical vector extends upwardly it has a direction of minus ninety degrees. Normally, a heart vector has a direction of between minus thirty degrees and one hundred five degrees. The axis corresponding to line I—I is the horizontal axis, the axis corresponding to line II—II passes through sixty and two hundred forty degrees, and the axis corresponding to line III—III passes through minus sixty and one hundred twenty degrees. Electrode sensors placed on a line parallel to the T-vector register an electrocardiographic signal with the largest T-wave component. Similarly, electrode sensors placed on a line parallel to the P-vector or the R-vector, Q-vector, or S-vector register the largest P-wave and QRS-wave deflection, respectively. The relationship between the position of the electrode sensors and the three axes therefore determine the magnitude of the P-, Q-, R-, S-, and T-wave deflections. Because the geometrically standardized sensor positions utilized in the prior art, and illustrated in FIG. 2, are positioned without regard to these axes, the waveforms detected by the sensors are completely dependent upon where the sensors are positioned. Referring now to the illustration of FIG. 4, there is shown an alternate geometry of positioning of electrocardiographic electrode sensors for using geometric standardization. Each of the electrode sensors 28 are preferably affixed along vertical lines 30 and 32 such that adjacent ones of the electrode sensors 28 are maintained at pre-determined spacings from one another. In the preferred embodiment of FIG. 4, lines 30 and 32 each contain eight sensors 28, with adjacent ones of the sensors 28 being spaced at known distances from one another. Each electrode sensor on lines 30 and 32 may be identified by sequential numerals $L_1$, $L_2$, ... $L_8$, and $R_1$, $R_2$, ... $R_8$. Positioning the electrode sensors 28 on the bands to form the geometry of FIG. 4 is preferred over the standard geometry of FIG. 2, since the electrode sensors can be quickly applied to an individual, as shown in FIG. 4, in order to perform diagnostic functions.

Use of the axis system of FIG. 3 to describe current vectors formed between sensors 28 of the geometry of FIG. 4 is shown in FIGS. 5A-B. FIG. 5A illustrates a current vector extending in a direction of approximately thirty degrees; as created by electrode sensor pair combination $R_4$ - $L_3$; FIG. 5B illustrates a current vector extending in a direction of approximately minus thirty degrees as created by electrode sensor pair combination $R_3$ - $L_4$.

Turning now to the block diagram of FIG. 6 there is illustrated in block form, the circuit utilized to select physiologically standardized sensor sets. Each of the electrode sensors 28 are electrically coupled to waveform measuring means 36 such that waveform measuring means 36 receives the signals sensed by the electrode sensors. Waveform measuring means 36 measures the magnitudes of the P-, Q-, R-, S-, and T-wave components of each of the detected waveforms. Each of the values measured by waveform measuring means 36 is supplied to averaging means 38. Averaging means 38 sums the measured values over a desired number of heartbeats to determine average values of the waveform components. The summing function is illustrated in the Figure by block 38A, and the average value of the summed signal is obtained by dividing the summed signal by the summing period, here illustrated by block 38B. Each of the average values obtained by averaging means 38 is supplied to comparator means 40. Comparator means 40 compares the average values of the magnitudes of the component waves of each of the waveforms and selects the waveforms (and hence the electrode sensors sets from which the waveforms are obtained) having the maximum P-wave components, Q-wave components, R-wave components, S-wave components, and T-wave components, respectively. In some instances, the same waveform contains two, or more, component waves having the maximum values. These signals are supplied to display means 42 to visually identify the waveforms and the electrode sensor sets L - R from which the waveforms are detected or any of many other external devices. These waveforms may then be utilized as the physiologically standardized waveforms from which diagnosis and analysis of an individual's cardiac performance is determined.

While the present invention has been described in connection with the preferred embodiments shown in the various figures, it is to be understood that other similar embodiments may be used or modifications and additions may be made to the described embodiment for performing the same functions of the present invention without deviating therefrom. For example, current vectors may be determined relative to the Einthoven triangle rather than the axis system illustrated in FIG. 3. Therefore, the present invention should not be limited to any single embodiment, but rather construed in breadth and scope in accordance with the recitation of the appended claims.

What I claim is:

1. Electrocardiographic apparatus for selecting a desired number of physiologically standardized sensors of a plurality of electrocardiogram sensors for forming leads to allow diagnosis of cardiac performance of an individual, said apparatus including:
   a plurality of electrocardiogram sensors for positioning on the individual and for sensing electrocardiogram waveforms indicative of cardiac functioning of the individual;
   waveform measuring means coupled to receive the electrocardiogram waveforms sensed by each of the leads formed by the electrocardiogram sensors of the plurality of electrocardiogram sensors for measuring magnitudes of predetermined components of the electrocardiogram waveforms;
   comparator means for comparing the magnitudes of the predetermined components of the electrocardiogram waveforms and for selecting the waveforms, and hence, the leads from which the electrocardiogram waveforms are sensed containing the predetermined components of the greatest magnitudes, said positions forming the leads on the individual corresponding to the physiologically standardized electrocardiogram sensor positions; and
   means for displaying said electrocardiogram waveforms selected by the comparator means.

2. The electrocardiographic apparatus of claim 1 wherein said waveform measuring means measures the magnitudes of the predetermined components during successive heartbeats and forms average values of the magnitudes of the predetermined components of each of the electrocardiogram waveforms displaying said electrocardiogram waveforms selected by the comparator means.

3. The electrocardiographic apparatus of claim 2 wherein said comparator means compares the average values formed by the waveform measuring means and selects the electrocardiogram waveforms containing the average predetermined components of the greatest magnitudes.

4. The electrocardiographic apparatus of claim 1 wherein said predetermined components measured by the waveform generating means includes T-wave components of the electrocardiogram waveform.

5. The electrocardiographic apparatus of claim 1 wherein said predetermined components measured by the waveform measuring means includes P-wave components of the electrocardiogram waveform.

6. The electrocardiographic apparatus of claim 1 wherein said predetermined components measured by the waveform measuring means includes R-wave components of the electrocardiogram waveform.

7. The electrocardiographic apparatus of claim 1 wherein said plurality of electrocardiogram sensors are positioned to form two vertically extending arrays for positioning on a chest area of the individual.

8. The electrocardiographic apparatus of claim 1 wherein said predetermined components measured by the waveform measuring means includes Q-wave components of the electrocardiogram waveform.

9. The electrocardiographic apparatus of claim 1 wherein said predetermined components measured by the waveform measuring means includes S-wave components of the electrocardiogram waveform.

10. A method for obtaining a physiologically standardized electrocardiogram sensor position to allow diagnosis of cardiac performance of an individual from a pair of electrocardiogram sensors, comprising the steps of:

positioning a plurality of electrocardiogram sensors on the individual for sensing electrocardiogram waveforms indicative of cardiac functioning of the individual;

measuring magnitudes of predetermined components of the electrocardiogram waveforms detected by each of the plurality of electrocardiogram sensors;

comparing magnitudes of the predetermined components of the electrocardiogram waveforms sensed by the electrocardiogram sensors; and selecting the electrocardiogram sensor pairs corresponding with electrocardiogram waveforms having the P-, Q-, R-, S-, and T-wave components of the greatest magnitudes as standardized electrocardiogram sensors, and the position thereof as the physiologically standardized electrocardiogram sensor position.

11. The method of claim 10 wherein said step of positioning includes positioning said plurality of electrocardiogram sensors to form two vertically extending lines on a chest area of the individual.

12. The method of claim 11 wherein said step of measuring includes measuring said magnitudes over successive heartbeats for forming average values of said magnitudes.

13. The method of claim 12 wherein said step of comparing includes comparing said average values of the magnitudes.

14. The method of claim 10 wherein said predetermined components includes P-wave components.

15. The method of claim 10 wherein said predetermined components includes R-wave components.

16. The method of claim 10 wherein said predetermined components includes T-wave components.

17. The method of claim 10 wherein said predetermined components includes Q-wave components.

18. The method of claim 10 wherein said predetermined components includes S-wave components.

* * * * *